United States Patent [19]

Rumer, Jr.

[11] 4,123,840
[45] Nov. 7, 1978

[54] PACKAGE FOR BLADES OR THE LIKE AND A METHOD OF ATTACHING SAME TO THE END OF A HANDLE

[75] Inventor: David O. Rumer, Jr., Rockford, Ill.

[73] Assignee: Richard-Allan Medical Industries, Inc., Richland, Mich.

[21] Appl. No.: 792,670

[22] Filed: May 2, 1977

[51] Int. Cl.² .................. B23P 11/02; B65D 83/10
[52] U.S. Cl. .................................. 29/453; 29/427; 206/363
[58] Field of Search .............. 29/453, 427; 206/363, 206/367, 370, 63.3

[56] References Cited

U.S. PATENT DOCUMENTS

| 1,387,839 | 8/1921 | Davis | 206/370 |
|---|---|---|---|
| 2,998,880 | 9/1961 | Ladd | 206/363 |
| 3,123,210 | 3/1964 | Hermanson et al. | 206/363 |
| 3,315,802 | 4/1967 | Lonholdt et al. | 206/363 X |
| 3,332,549 | 7/1967 | Powell | 206/363 |

*Primary Examiner*—Charlie T. Moon

*Attorney, Agent, or Firm*—Neuman, Williams, Anderson & Olson

[57] ABSTRACT

A package for a surgical blade or the like is provided which enables the blade to be readily attached to the elongated end of a handle without requiring the blade to be removed from the package during the manipulations attendant to the attachment. The package includes a flexible top panel and a flexible bottom panel which coact with one another to form an elongated blade-accommodating pocket having an opening therefor spaced from one end of the bottom panel. The accommodated blade has a slotted attachment end disposed adjacent the pocket opening. The handle end is inserted into the pocket opening between the blade and bottom panel and into the blade slot while the blade and associated panel portions are flexed a slight amount until the blade and handle end interlock with one another when the blade is returned to an unflexed condition and while the blade remains completely within the pocket. The handle end with the blade attached thereto is then withdrawn from the pocket out through the pocket opening.

7 Claims, 9 Drawing Figures

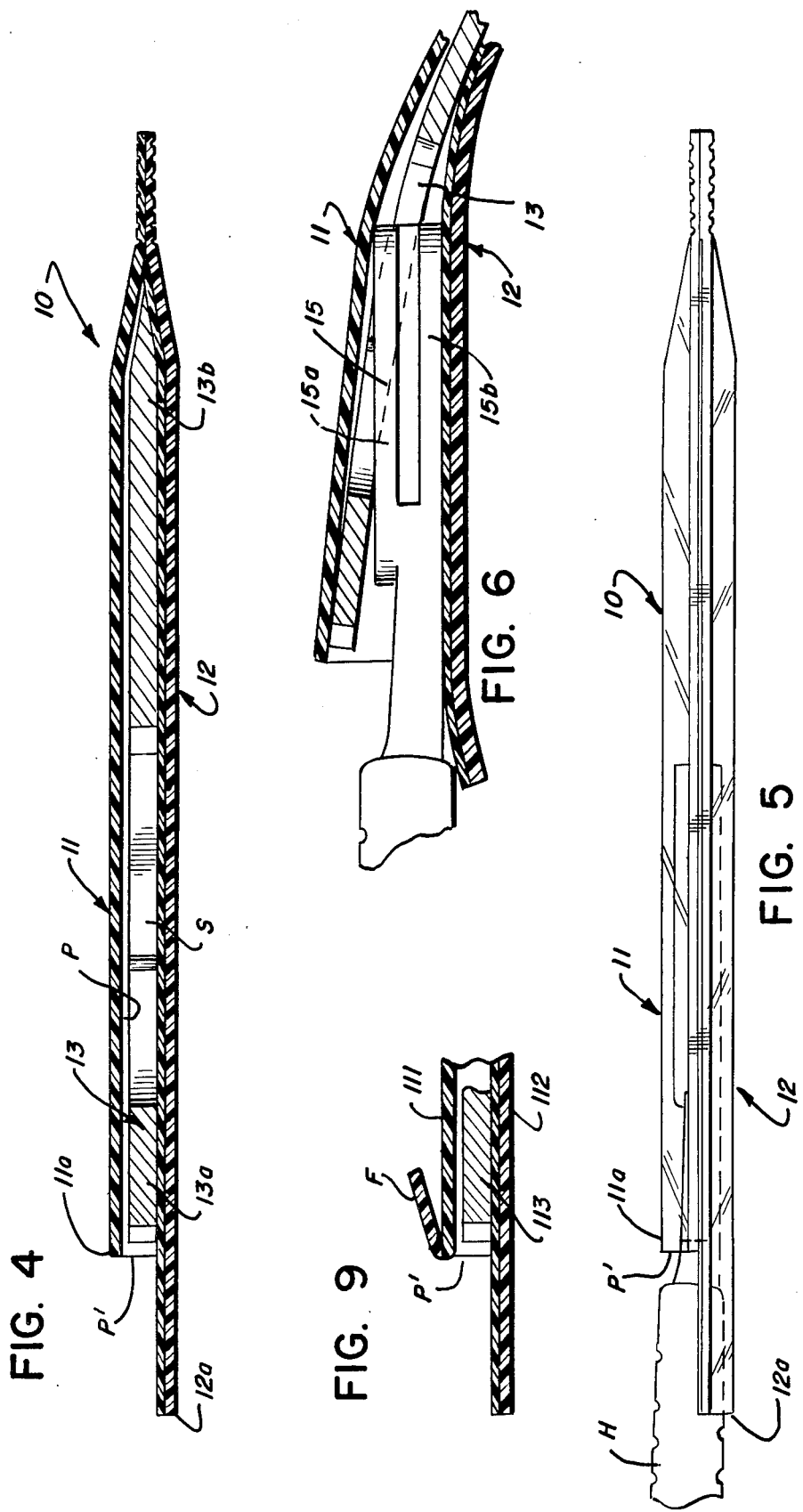

PACKAGE FOR BLADES OR THE LIKE AND A METHOD OF ATTACHING SAME TO THE END OF A HANDLE

BACKGROUND OF THE INVENTION

The procedure currently extant in most hospitals, clinics, and the like with regard to the rooms in which surgery is normally performed provides for the designation of adjacent sterile and unsterile areas in which personnel in one section do not have direct contact with personnel or equipment disposed in the other section while the surgery is in progress. In carrying out in one way such a procedure, sterile packages containing various materials (e.g., replaceable surgical blades) are opened in the unsterile area and without direct contact of the blades by the personnel in such area they are tossed or otherwise transferred onto a supporting surface located in the sterile area. Heretofore, it has been the practice for the exposed blade to be transferred to the sterile area. Subsequent to the exposed blade being located in the sterile area, the attending nurse or assistant picked up the blade from the supporting surface and with the exercise of extreme care and dexterity attached the blade to the end of a scalpel handle. Because the blades are thin and have very sharp cutting edges, the gloved hand of the nurse or assistant was frequently nicked by the blade or in some instances the hand was cut requiring replacement of the nurse or the assistant.

As an alternative way of carrying out the procedure, the package for the blade was opened in the unsterile area and the opened package held by the person in the unsterile area so that only the attachment end portion of the blade was exposed whereby the person in the sterile area could physically withdraw the exposed blade from the package without contacting the other package components or the person holding the package. Such a procedure, however, required good coordination between the personnel in the two areas. Frequently the transfer was delayed because one of the persons in one area was unavailable at a particular time because of the performance of other essential duties. Furthermore, unless care was exercised in opening the package in the unsterile area, the blade would fall out of the package and become unsterile and, thus, have to be discarded.

Various packages for surgical blades have heretofore been provided; however, because of certain inherent design characteristics they are possessed of one or more of the following shortcomings: (a) the package is of complex, costly and/or bulky construction; (b) the package is difficult and awkward to open; (c) the package is ineffective in providing protection for the person handling same in the normal manner during attachment of the blade to a handle; and (d) the blade must be removed from the package prior to being attached to the handle.

SUMMARY OF THE INVENTION

Thus, it is an object of the invention to provide a package of the type described which readily avoids the aforenoted shortcomings associated with prior packages of this general type.

It is a further object of the invention to provide such a package which is compact and may be readily bulk packed with like packages and yet preserve the sterile character of each individual package.

It is a further object of the invention to provide a package which is readily compatible to preserving the integrity of the sterile and unsterile areas in the area where surgery is or is to be performed.

It is a still further object of the invention to provide a package of the type described wherein certain components may be color coded, so that a given size and type of blade may be readily identified before the blade is removed from the package.

It is a still further object of the invention to provide a package wherein the attachment of the blade to the handle occurs while the blade remains within the package and yet, the attachment manipulations within the package may be observed.

It is a still further object of the invention to provide a package which may be readily formed and filled by high speed, automatic or semi-automatic equipment.

Further and additional objects will appear from the description, accompanying drawings and appended claims.

In accordance with one embodiment of the invention, a package of the type described is provided which includes a flexible top panel and a flexible bottom panel which coact with one another to form an elongated pocket open at one end. The pocket opening is spaced from one end of the bottom panel. A thin blade or the like, having an attachment end portion, is disposed within the pocket with the attachment end portion positioned adjacent the pocket opening whereby an elongated end of a handle may be inserted through the pocket opening and engage in interlocking relation the handle attachment end portion while the blade is completely disposed within the pocket. Once the blade is attached to the handle end portion, the handle end portion and attached blade are withdrawn as a unit from the pocket through the pocket opening.

DESCRIPTION

For a more complete understanding of the invention reference is made to the drawings, wherein:

FIG. 4 is an enlarged sectional view taken along line 4—4 of FIG. 3.

FIG. 5 is an enlarged side elevational view of the package of FIG. 3 and showing a handle end portion attached to a blade prior to the handle end portion and blade being withdrawn as a unit from the pocket.

FIG. 6 is an enlarged, fragmentary, sectional view similar to FIG. 4 but showing the blade and associated top and bottom panel portions being flexed a slight amount to facilitate attachment of the blade to the handle end portion.

FIG. 9 is an enlarged fragmentary sectional view similar to FIG. 4, showing the pocket opening formed in a modified package.

Figure 3:
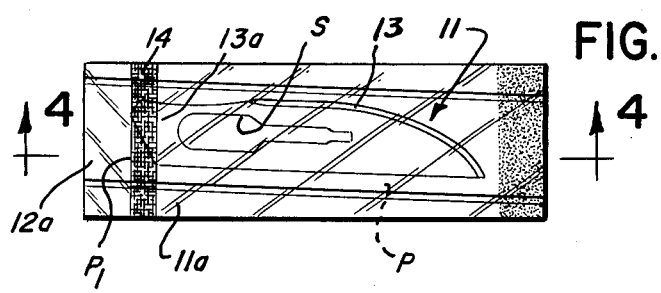
FIG. 3 is a top plan view of one form of the package per se.

Referring now to the drawings and more particularly to FIGS. 3 and 4, one form of the improved package 10 is shown wherein a top panel 11 and a bottom panel 12 are provided which coact with one another to form a suitable pocket P in which is disposed a thin, replaceable element 13 such as a surgical blade or the like. The top and bottom panels are preferably formed of thin flexible plastic sheet material and the corresponding three side edges of the panels are heat sealed or otherwise secured together. The length of the bottom panel 12 is greater than that of the top panel 11; thus, resulting in an opening P' to the socket P being formed by the free edge 11a of the top panel 11 and spaced from the corresponding end 12a of the bottom panel 12. To readily identify the opening P', a visually contrasting indicia (e.g., a stripe) 14 may be provided on the exterior of the panel 11; the indicia being adjacent to and co-extensive with the edge 11a of the top panel 11. The remainder of top panel 11 is preferably transparent so that the blade 13 may be readily observed when it is disposed within the pocket.

The bottom panel 12 is preferably opaque and color coded so that the type and size of blade 13 accommodated in the pocket may be readily determined from a distance without having to remove the blade from the package or observing same through the transparent top panel 11.

The blade 13 is of conventional design and is formed of high grade sheet metal. One end portion 13a of the blade in the illustrated embodiment is narrowed a slight amount and is adapted to engage and interlock with an elongated end portion or tang 15 of a scalpel handle H or the like. The handle and the tang thereof are of conventional design and per se form no part of the invention herein disclosed. Formed on one side of the tang 15 is an elongated protuberance or hump 15a. Partially encircling the underside of the hump is a groove 15b having a size capable of accommodating portions of the blade which define an elongated slot S, see FIG. 3. Once the hump 15a has been properly positioned within the blade slot S, in a manner to be hereinafter described, the blade and tang are in interlocking relation and can be removed as a unit from the pocket P.

Figure 7:
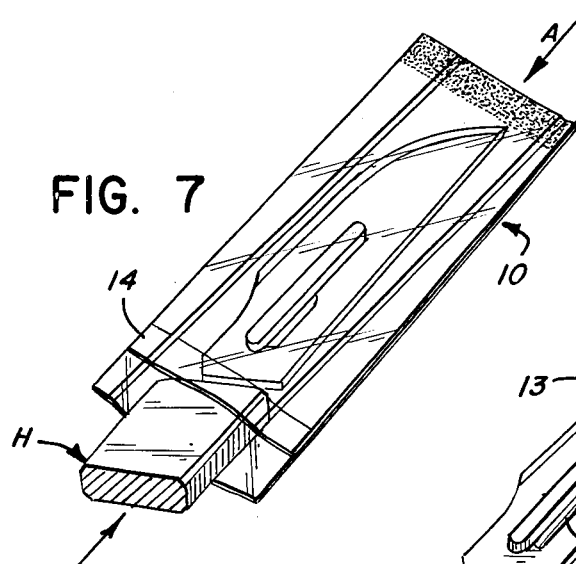
FIGS. 7 and 8 are top perspective views of the package of FIG. 3 showing, respectively, the relative movement of the package and handle end portion to effect attachment of the blade to the handle end portion, and removal of the handle end portion and attached blade as a unit from the pocket.
Figure 8:
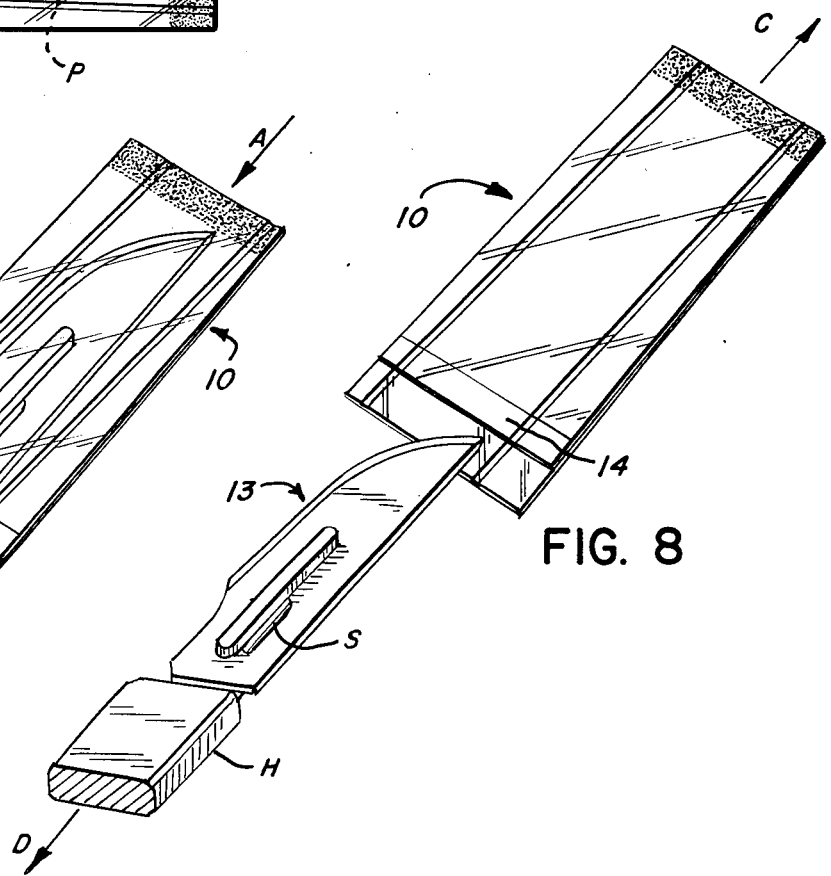

In attaching the tang to the blade 13, the closed end portion of the package 10 is firmly grasped between the fingers of the nurse or assistant with the top panel 11 facing upwardly so that the opening P' to the pocket is exposed. The tang 15 of the handle H is then inserted through the opening P' between the blade and bottom panel 12. The leading end 13b of the blade (that is the end opposite the attachment end 13a) and associated portions of the panels 11 and 12 are bent downwardly a slight amount so as to present a slightly concave surface to the leading end of the tang, thereby facilitating entry of the hump 15a into the narrowed portion of the slot S, see FIG. 6. Simultaneously with the bending of the blade leading end 13b and associated panel portions, the package is moved in a direction, see arrow A in FIG. 7, which is opposite to the direction, see arrow B, of movement of the tang 15. As aforementioned, the groove 15b beneath the hump is shaped so as to slidably accommodate the portions of the blade defining the narrow section of the slot. Once the hump has been inserted to the fullest extent within the blade slot S, the blade end portion 13b and associated panel portions are released, causing the blade to return to its planar state and snap into interlocking relation with the tang. As seen in FIG. 8, the package is then moved in direction C while the tang and attached blade are moved in the opposite direction D thereby enabling the blade and tang to be readily withdrawn as a unit from pocket P through opening P'. It is important to note that attachment of the blade to the tang and the withdrawal of same from the pocket are accomplished without any direct physical contact between the blade and the hand of the nurse or assistant, thus, preserving the sterile condition of the blade and at the same time minimize the hazards associated with such manipulations.

As seen in FIG. 9, the edge 111a of the top panel 111 of a modified form of package 110 is provided with a short foldable flap F which is substituted for the visual contrasting stripe 14 previously described with respect to FIG. 3. The flap is initially folded over the exposed surface of the top panel 111 of the package 110 when the latter is initially sandwiched between a pair of laminae 16 and 17 which comprises an outer protective sleeve 18, see FIGS. 1 and 2. When the package 111 is removed from sleeve 18, the inherent fightback of the panel sheet material will cause the flap F to automatically assume an angular, upwardly extending position as seen in FIG. 9. The flap in such a position may be readily grasped by the fingers of the nurse or assistant and thereby facilitate picking up the package from a flat supporting surface.

Figure 1:
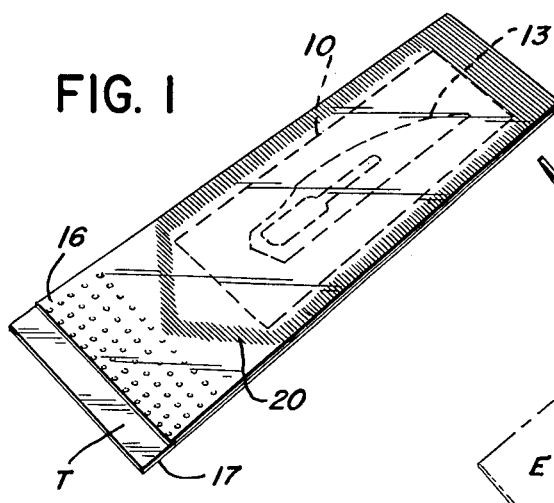
FIG. 1 is a perspective view of one form of the package shown disposed within an outer protective sleeve.
Figure 2:
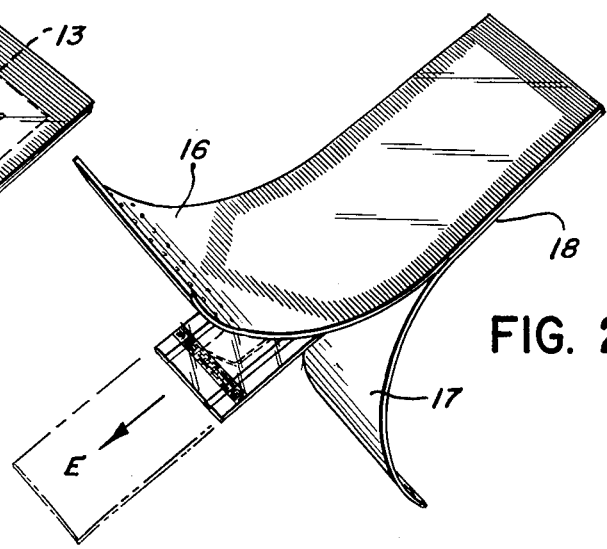
FIG. 2 is similar to FIG. 1 but showing laminae of the protective sleeve being separated so that the whole package is expelled from the interior of the outer sleeve without the package itself being physically contacted by the person opening the sleeve.

The outer protective sleeve 18 as seen in FIGS. 1 and 2 may be formed of foil laminae 16 and 17 which have corresponding portions thereof crimped, fused or otherwise secured together so as to form an endless seal 20 which completely encircles the package 10 or 110 disposed between the laminae 16 and 17. The area delimited by the seal is slightly larger than the periphery of the package 10 or 110. This is an important feature so that the whole package can be expelled from the sleeve when the laminae 16 and 17 are separated from one another as will be hereinafter explained.

As seen in FIG. 1, lamina 17 has a slightly greater length than lamina 16, so as to form a finger tab T which is spaced outside of the area delimited by seal 20. The tab T facilitates peeling apart the laminae when the package 10, 110 is to be removed from the sleeve 18. Upon the laminae being peeled apart quickly by a person standing in the unsterile area the package 10, 110 will be propelled therefrom in direction (arrow E, FIG. 2) onto a supporting surface, not shown, which is located in a sterile area without the package itself being physically contacted or touched by a person within the unsterile area.

The package is assembled within the sleeve 18 prior to the package and accommodated blade being subjected to sterilizing temperatures in a manner well known in the art. Assemblying the blade between the panels 11 and 12 and subsequently sandwiching the package between the laminae 16 and 17 may be readily accomplished by utilizing high speed automatic or semi-automatic packaging equipment known in the art.

While the package has been described and illustrated in relation to a replaceable blade, it is not intended to be limited thereto, as other types of thin replaceable elements, either in a sterile or unsterile state, may be accommodated within the pocket provided one end of the element is adjacent the pocket opening and is suitable for attachment to an inserted tang of a handle. The size and shape of the pocket and the opening therefor will depend on the configuration of the accommodated element.

Thus, it will be seen that an improved package has been provided which is of simple and compact construction, and is capable of enabling a blade or like element to be readily attached to the tang of a handle while the blade or like element remains enclosed within the pocket. The improved package eliminates, or significantly reduces, the hazards heretofore associated with attaching a surgical blade to a scalpel handle. The improved package is also most compatible with the practice presently being followed by hospitals and the like in preserving the sterile integrity of the area in which surgery is being performed.

I claim:

1. A package comprising an elongated bottom panel; and elongated top panel overlying same, said top panel having elongated opposite side peripheral portions and one end peripheral portion attached to said bottom panel and coacting therewith to form an elongated pocket, an opposite end peripheral portion of said top panel having a segment thereof unattached and forming an opening to said pocket, said panels being formed of flexible sheet material, said opening being spaced inwardly from a peripheral end of said bottom panel; and a thin elongated replaceable element slidably positioned with said pocket, said element having an attachment end portion disposed within the pocket and adjacent said pocket opening and being adapted to be engaged by and connected to a complemental handle segment subsequent to the latter being inserted through the pocket opening upon distorting of at least one of the pocket-forming panels and while the entire element is enclosed within the pocket.

2. The package of claim 1 wherein one of the panels is color coded.

3. The package of claim 1 wherein the length of the top panel is shorter than the length of the bottom panel and one end of the top panel is spaced from the corresponding end of said bottom panel and coacts therewith to define the opening to the pocket.

4. The package of claim 1 wherein said package is sealed within an outer sleeve adapted to be manually opened at one end whereby simultaneously therewith the whole package is expelled therefrom without said package and the element disposed therein being manually contacted during opening of the outer sleeve.

5. The package of claim 4 wherein the edge of the top panel adjacent the pocket opening is provided with identifying means.

6. The package of claim 5 wherein the identifying means includes an external flap foldably connected to the segment of the top panel adjacent the pocket opening, said flap being adapted to project over a portion of the exterior surface of the top panel.

7. A method of attaching a tang of a handle to the attachment end of a thin resiliently flexible surgical blade while the latter is completely disposed within a pocket formed between a flexible elongated top panel and a flexible elongated bottom panel, the pocket having an opening thereto formed adjacent to but spaced from an end of the bottom panel, the attachment end of the blade being disposed within the pocket adjacent the pocket opening; said method comprising inserting the tang into the pocket and between the blade and one of the panels, sliding the tang into engagement with the attachment end of blade while the blade and attachment end are completely enclosed within the pocket, manipulating the blade and tang to effect interlocking of the tang and blade attachment end within the pocket and withdrawing as a unit the tang with the blade attached thereto out through the pocket opening.

* * * * *

UNITED STATES PATENT AND TRADEMARK OFFICE
CERTIFICATE OF CORRECTION

PATENT NO. : 4,123,840
DATED : November 7, 1978
INVENTOR(S) : David O. Rumer, Jr.

It is certified that error appears in the above-identified patent and that said Letters Patent are hereby corrected as shown below:

Column 3, line 15, "socket" should be -- pocket --

Column 5, line 17, "and" should be -- an --

Signed and Sealed this

Twenty-seventh Day of March 1979

[SEAL]

Attest:

RUTH C. MASON
Attesting Officer

DONALD W. BANNER
Commissioner of Patents and Trademarks